(12) United States Patent  
Patoureaux et al.

(10) Patent No.: US 7,693,255 B2  
(45) Date of Patent: Apr. 6, 2010

(54) COMPRESSION PAD AND MAMMOGRAPHY APPARATUS COMPRISING SUCH A PAD

(75) Inventors: Fanny Patoureaux, Beynes (FR); Jean-Claude Ledan, Romorantin (FR); Alain Rauby, Gif S/Yvette (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/361,560

(22) Filed: Jan. 29, 2009

(65) Prior Publication Data

US 2009/0196394 A1 Aug. 6, 2009

(30) Foreign Application Priority Data

Jan. 31, 2008 (FR) .................................. 08 50613

(51) Int. Cl.  
*A61B 6/04* (2006.01)

(52) U.S. Cl. .......................................... 378/37; 378/195

(58) Field of Classification Search ................... 378/37, 378/208, 195, 196  
See application file for complete search history.

(56) References Cited

U.S. PATENT DOCUMENTS

2005/0036584 A1 2/2005 Lebovic et al.  
2006/0126794 A1* 6/2006 Hermann et al. ............ 378/180

FOREIGN PATENT DOCUMENTS

EP            1149559 A    10/2001  
WO    WO 2005/046429 A    5/2005

\* cited by examiner

*Primary Examiner*—Hoon Song  
(74) *Attorney, Agent, or Firm*—Global Patent Operation; Jonathan E. Thomas

(57) ABSTRACT

Compression pad for a mammography apparatus comprising a compression plate made of a material transparent to X-rays, and a support by which said pad is configured to be mounted onto a mammography apparatus. The support has an arch shape configured to go over the edge of a compression plate, and said compression plate and said support comprise complementary mechanical means capable of enabling manual locking/unlocking of the support on said plate, in particular for cleaning said plate and said support.

10 Claims, 4 Drawing Sheets

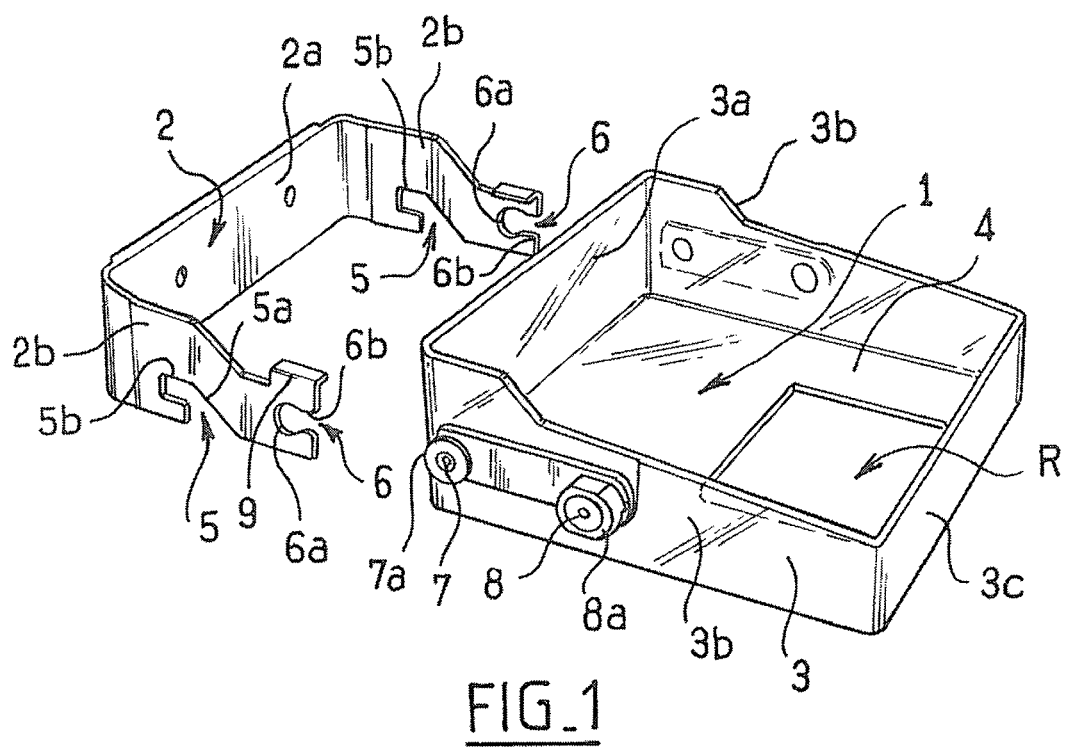
FIG_1
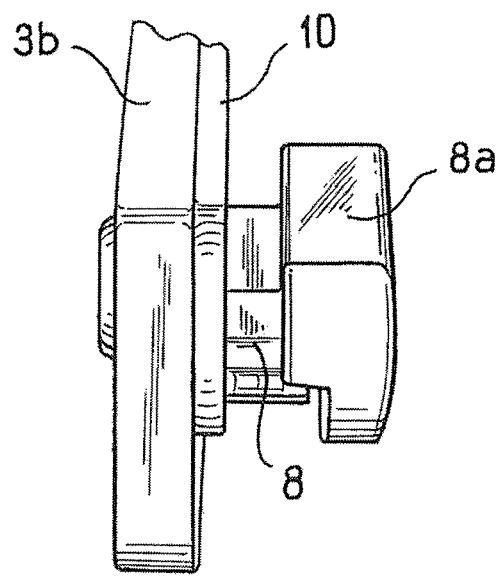
FIG_2

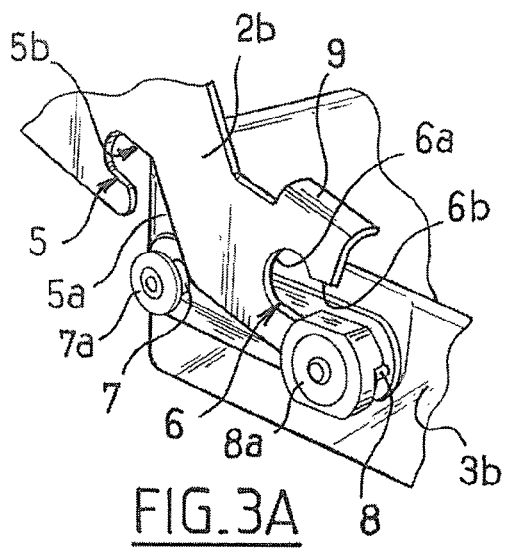
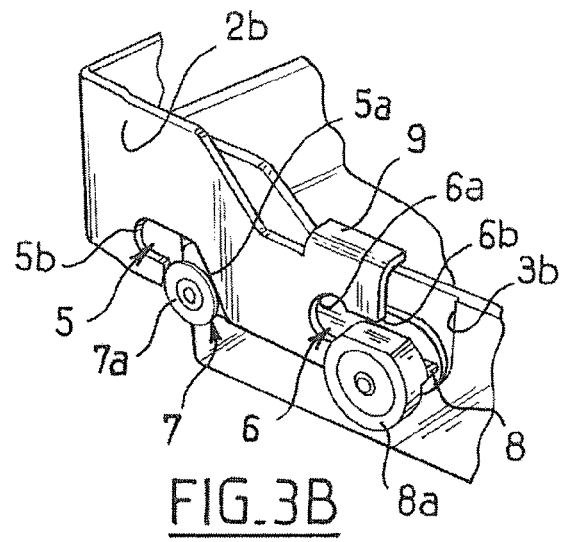
FIG_3A
FIG_3B
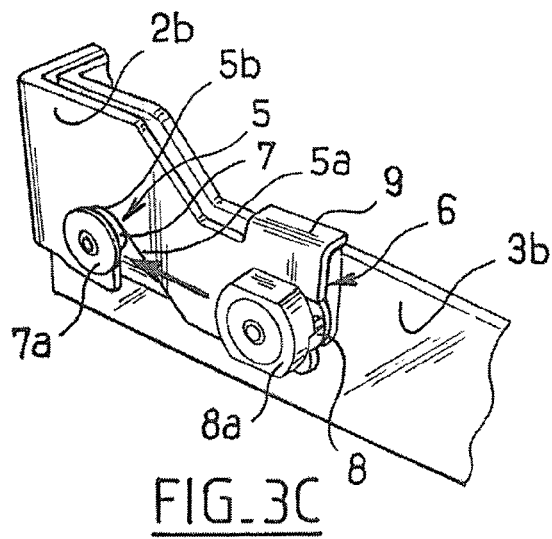
FIG_3C
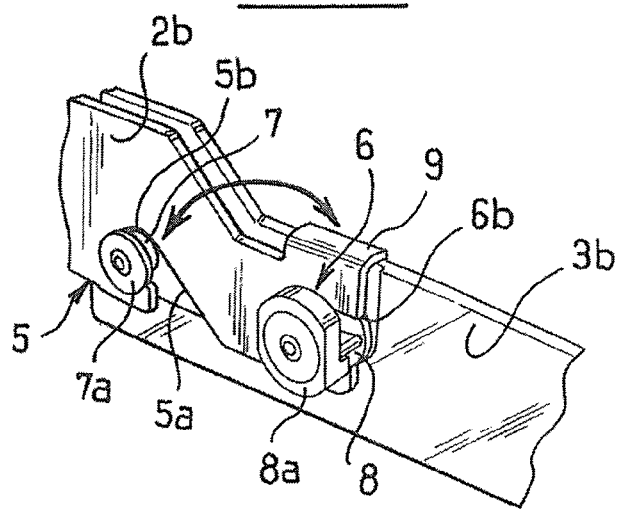
FIG_3D

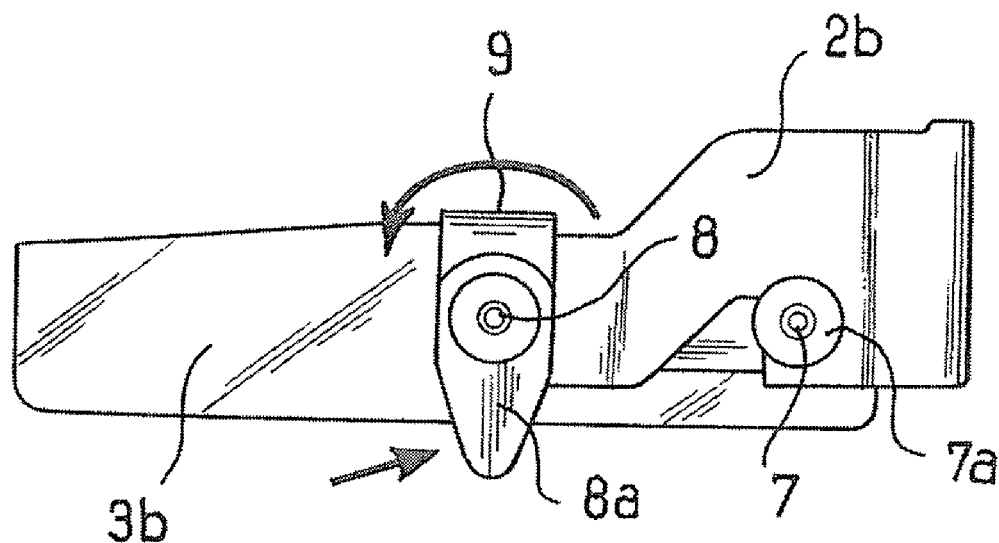
FIG_4A
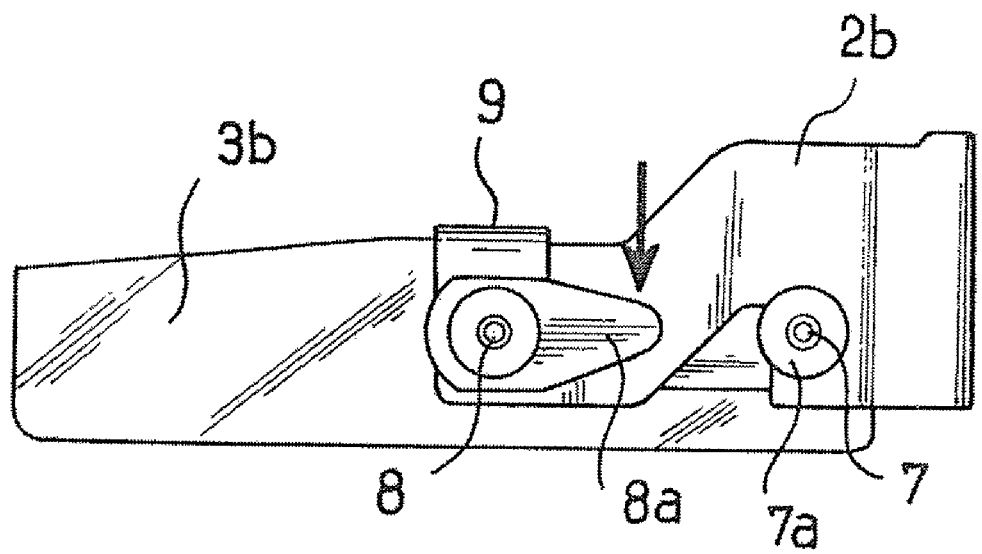
FIG_4B

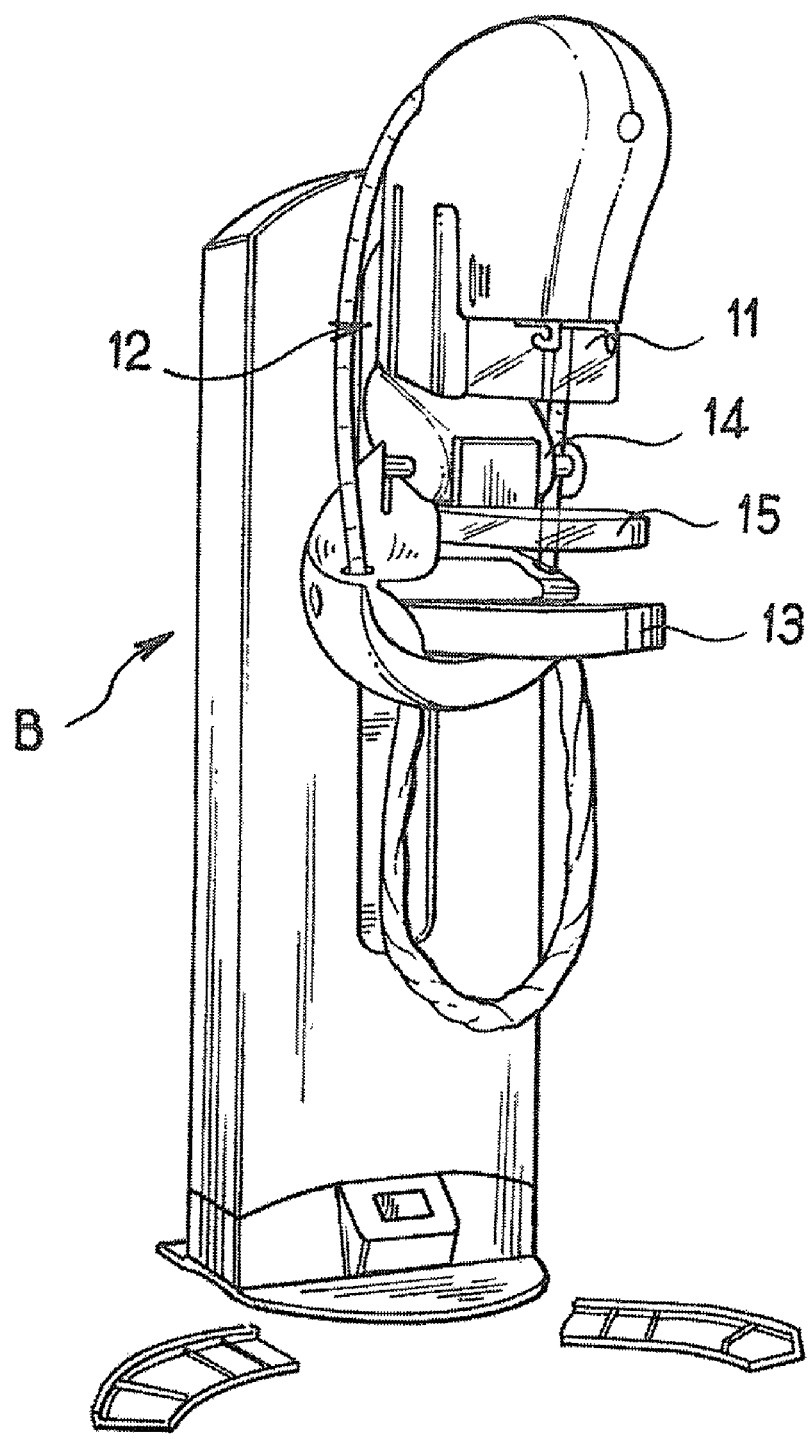
FIG_5

COMPRESSION PAD AND MAMMOGRAPHY APPARATUS COMPRISING SUCH A PAD

CROSS-REFERENCE TO RELATED APPLICATIONS

This application claims priority under 35 U.S.C. §119(a)-(d) or (f) to prior-filed, French patent application serial number 0850613, filed on 31 Jan. 2009, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

The field of the invention relates to medical imaging and more specifically to mammography techniques. It relates in particular to a compression pad for a mammography apparatus, as well as a mammography apparatus including such a pad.

2. Description of Related Art

Mammography apparatuses conventionally include at least one source of X-rays and a console, arranged opposite said source and configured to receive and support the patient's breast. This console includes a sensor for sensing X-rays after they have passed through the patient's breast (array of sensors, film cassette sensitive to X-rays, etc.) and has a compression plate—also called a pad—capable of compressing the breast against the console during imaging.

Mammography apparatuses in this sense include, for example, those that the GE Medical Systems company proposes under the name "Senographe" (registered trademark). A detailed example of the structure of such an apparatus is also described in the U.S. Pat. No. 4,979,196.

Normally, a compression pad for a mammography apparatus comprises a compression plate made of a material transparent to X-rays, attached to a support, for example in the form of an arch. This support is itself hooked onto means of the mammography apparatus that make it possible to translate the compression pad in the direction of the X-rays, so as to compress the patient's breast between the console and said pad.

Usually, the two parts that constitute, on the one hand, the compression plate made of a material transparent to X-rays and, on the other hand, the support are attached to one another, for example by rivet-type means.

BRIEF SUMMARY OF THE INVENTION

It is of course desirable to be capable of using compression pads for interventional examinations (biopsies, for example). However, it is possible then that deposits, for example, blood, will spill onto the pad.

Compression pads with rivets present problems in this regard, because the rivets can constitute retention areas that are difficult to access when cleaning the pad.

An embodiment of the invention therefore provides a compression pad that is easy to clean and that in particular does not have any inaccessible areas.

In particular, it provides a pad structure in which the compression pad and its support can easily be separated, and the pad can be disassembled and reassembled manually without requiring complicated handling, and in particular without requiring tools. The compression pad and the support can then easily be cleaned separately, without there being any inaccessible areas on said support and on said plate (at least on the face thereof that contacts the breast).

More specifically, an embodiment of the invention provides a compression pad for a mammography apparatus comprising a compression plate made of a material transparent to X-rays and a support by which said pad is configured to be mounted onto a mammography apparatus, wherein the support and the compression plate are capable of being manually separated from one another, particularly for separate cleaning.

In particular, in an advantageous embodiment, the support has an arch shape configured to go over the edge of a compression plate, wherein said compression plate and said support are configured to enable manual locking/unlocking of the support on said plate.

BRIEF DESCRIPTION OF THE FIGURES

Other features and advantages of embodiments of the invention will become clear from the following description, which is purely illustrative and non-limiting and must be read in reference to the appended drawings, in which:

FIG. 1 diagrammatically shows a perspective view of a compression pad according to a possible embodiment of the invention, after separation of the support and the transparent compression plate;

FIG. 2 shows a side view of a possible embodiment for a portion of the anchoring means on the transparent compression plate of the pad of FIG. 1;

FIGS. 3A, 3B, 3C and 3D show four steps for installing the plastic part of the pad of the preceding figures;

FIGS. 4A and 4B are two side views showing another possible embodiment for the anchoring means;

FIG. 5 diagrammatically shows a mammography apparatus comprising a pad according to one of the embodiments of the preceding figures.

DETAILED DESCRIPTION OF THE INVENTION

The compression pad shown in FIG. 1 comprises a compression plate 1 and a support 2 attached thereto. This support 2 is itself suitable for being attached to means forming the lever of the mammography apparatus.

The support 2 is, for example, metal, or made of a plastic or composite material and more generally any other material allowing for resistance compatible with its support function.

The compression plate 1 is made of a material transparent to X-rays. It is in the form of a base 4, which has a generally rectangular shape and which extends, on each of its four sides, by an edge 3 that surrounds said base 4. The edge 3 comprises a front wall 3a, (at the level of the part of said plate 1 that receives the support 2), two lateral walls 3b and a rear wall 3c. The front wall 3a and portions of the two lateral walls in the immediate extension of said front walls have a greater height than the rest of said edge 3, i.e. than the rest of the two lateral walls 3b and the rear wall 3c.

In addition, the base 4 has, on the side opposite the front wall 3a of the edge 3, an opening R, for example rectangular, configured in particular to allow the passage of a biopsy tool in a step following the imaging and the analysis of the images by the practitioner.

Other opening shapes are of course possible, for example a multitude of circular through-shapes distributed over the surface of the compression plate.

The support 2 has a U-arch shape that is configured to go over the edge 3 at the level of the front part of the plate 1, being pressed on the front wall 3a and bordering the lateral walls 3b so as to be anchored there.

This support 2 has:

a base 2a that, when the arch is in position on the edge 1b, is pressed on the higher front wall 3a, and two lateral branches 2b that each comprise notches 5 and 6 that cooperate with complementary means on the lateral walls 3b of the edge 3 so as to removably anchor the support 2 on the compression plate.

More specifically, on each of the branches 2b, the notch 5—which is the one closest to the base 2a—is a hole formed on said branch 2b, from a longitudinal section thereof, so as to define a guide ramp 5a inclined with respect to the general direction of the branch 2b, and a recess 5b configured to receive a complementary pin 7 on the corresponding lateral wall 3b.

The notches 6 are formed at the ends of the branches 2a and have an oblong recess shape 6a leading to the end section of the branch 2b through an opening 6b forming a narrow neck. The main direction of the oblong recesses 6a is perpendicular to the direction in which the branches 2b extend.

These notches 6 are configured to receive locking pins 8 with an oblong or flattened cross-section (FIG. 2) rotatably mounted on the branches 2b between a position in which the notches 6 can be introduced on said pins 8 by the narrow neck 6b and a locking position in which said pins with an oblong or flattened cross-section 8, after having been placed in the oblong recesses 6a, are turned a quarter turn in order to lock the branches 2b on the lateral walls 3b.

As regards the anchoring means on the lateral walls 3b of the edge 3, the pins 7 and 8 end with rollers 7a and 8a to which they are rigidly attached. These rollers are spaced from the lateral wall 3b on which they are mounted with a thickness slightly greater than that of the branches 2b of the support 2.

These pins 7 and 8 are attached by riveting to the lateral walls 3b, with a metal plate 10 being provided on each wall 3b so as to reinforce said wall and enable said riveting. It is noted that the rivets are located on the side of the compression pad opposite the side that receives the breast, and are protected from any soiling by the edge 3 that surrounds the plate 1.

Other means for attaching the pins 7 and 8 to the walls 3b are of course possible: for example, bonding, welding (in the case of compatible materials), snapping, etc.

The branches 2b end, plumb over the notches 6 and at the level of their sections opposite that where the notches 5 open out, with contact edges 9 perpendicular to the general plane of said branches and lateral walls 3b.

The placement of the support 2 on the plate 1 is performed as follows.

The branches 2b of the support 2 are presented on the flattened locking pins 8, by causing said branches 2b to glide along the walls 3b, and introducing the notches 6 on the pins 8 through their narrow-neck openings 6b, with a certain inclination (FIG. 3A). In this step, the rollers 8a help to guide the movement of the branches 2b.

Once the notches 6 are in place at the level of the flattened pins 8, the user tilts the branches 2b of the support 2, coming into contact with the edges 9 and folds back said branches on the lateral walls (FIG. 3B). Then, the user continues the movement so as to approach the base 2a of the front wall 3a, by causing the ramps 5a of the two branches to glide on the two pins 7.

When the end of the ramp is reached, the user pushes the support 2 so that the base 2a is positioned on the front wall 3a (FIG. 3C). The pin 7 is then housed in the recess 5b, while the pin with an oblong or flattened cross-section 8 is positioned in the recess 6a.

In a final step, the user turns the rollers 8a and their flattened pins 8 one quarter turn, thus locking the support 2 on the compression plate 1.

The compression pad is then ready to be used on the mammography apparatus.

Similarly, after use, said compression plate and its support can easily be separated so as to be cleaned separately from one another by performing the reverse of the operations described above.

As understood, such a structure no longer has a gap (on its portion in contact with the breast and in particular between the support and the compression plate) that would not be easy to clean after disengagement of the support with respect to the compression plate.

Another alternative of the invention is shown in FIGS. 4A and 4B. In this alternative, the rollers 8a that the operator grips to lock the axes 8 have an elongate shape that facilitates the handling by the operator. In addition, when the operator places the support on the compression plate, these gripping rollers 8a extend initially substantially perpendicularly with respect to the compression plate 1 and go beyond the edge 3 thereof. In this way, the user is led to fold them back manually, thus necessarily ensuring the locking of the support the plate.

FIG. 5 diagrammatically shows a mammography apparatus that includes, on a frame B, an X-ray source 11 mounted on a support 12. A console 13 housing radiosensitive means (film cassette, electronic array receiver) is arranged opposite the source 11.

The frame B also has a mobile compression arm 14 on which a compression pad of the type described above can be placed (pad 15 in FIG. 5), for example by placing the base 2a of the support 2 in a complementary track provided on the arm 14. This arm 14 is itself powered and is driven, for example by means of a rack system, in a translation movement that moves the pad 15 toward or away from the console 13, so as to compress or decompress the breast undergoing radiography.

With the compression pad structure described above, after use, it is possible to disassemble the pad 15 and to separate the compression support from the compression plate, so that the user can thoroughly clean both parts.

The invention claimed is:

1. A compression pad for a mammography apparatus, the compression pad comprising:

a compression plate made of a material transparent to X-rays;

pins coupled to an edge of the compression plate, the pins comprising a guide pin, and a locking pin having an oblong or flattened cross-section; and a support configured to mount the compression pad onto the mammography apparatus, the support having an arch shape with two branches configured to go over the edge of the compression plate, each branch having at least one notch for receiving the guide pin, and at least one notch for receiving the locking pin, wherein the support and the compression plate are configured to enable manual separation of the support and the compression pad.

2. The compression pad of claim 1, wherein one or more of the pins and the notches are further configured to enable manual locking/unlocking of the support on the compression plate.

3. The compression pad of claim 2, wherein the
the notch for receiving the locking pin has a opening forming a narrow neck for locking the branch on the locking pin by pivoting the locking pin to a locking position.

4. The compression pad of claim 3, wherein each of the branches of the support has, at one end, a contact edge configured to pivotably guide its respective branch with respect to the edge of the compression plate when the opening is positioned on the locking pin.

5. The compression pad of claim 3, wherein the locking pin ends with an elongate gripping roller.

6. A mammography apparatus, comprising:
a radiation source;
a sensor disposed opposite the radiation source; and
a compression pad configured to be interposed between the radiation source and the sensor, wherein the compression pad comprises:
 a compression place made of a material transparent to X-rays;
 pins coupled to an edge of the compression plate, each of the pins comprise a guide pin, and a locking pin that has an oblong or flattened cross-section; and
 a support configured to mount the compression pad onto a mammography apparatus, the support has an arch shape with two branches configured to go over the edge of the compression plate, each branch has at least one notch that receives the guide pin, and at least one notch that receives the locking pin,
 wherein the support and the compression plate are configured to enable manual separation of the support and the compression pad.

7. The compression pad of claim 6, wherein one or more of the pins and the notches are further configured to enable manual locking/unlocking of the support on the compression plate.

8. The compression pad of claim 7, wherein
the notch for receiving the locking pin has a opening forming a narrow neck for locking the branch on the locking pin by pivoting the locking pin to a locking position.

9. The compression pad of claim 8, wherein each of the branches of the support has, at one end, a contact edge configured to pivotably guide its respective branch with respect to the edge of the compression plate when the opening is positioned on the locking pin.

10. The compression pad of claim 8, wherein the locking pin ends with an elongate gripping roller.

\* \* \* \* \*

UNITED STATES PATENT AND TRADEMARK OFFICE
CERTIFICATE OF CORRECTION

PATENT NO. : 7,693,255 B2
APPLICATION NO. : 12/361560
DATED : April 6, 2010
INVENTOR(S) : Patoureaux et al.

It is certified that error appears in the above-identified patent and that said Letters Patent is hereby corrected as shown below:

In Column 1, Line 8, after "prior-filed," insert -- co-pending --.

In Column 1, Line 9, delete "2009," and insert -- 2008, --, therefor.

In Column 5, Line 11, in Claim 3, after "wherein" delete "the".

In Column 5, Line 28, in Claim 6, delete "place" and insert -- plate --, therefor.

Signed and Sealed this
Eleventh Day of January, 2011

David J. Kappos
*Director of the United States Patent and Trademark Office*